United States Patent [19]

Leveen et al.

[11] Patent Number: 5,000,750
[45] Date of Patent: Mar. 19, 1991

[54] DEVICE FOR THE TREATMENT OF FECAL IMPACTION

[75] Inventors: Robert F. Leveen; Eric G. Leveen, both of Charleston, S.C.

[73] Assignee: Device Developments, Inc., Las Vegas, Nev.

[21] Appl. No.: 284,128

[22] Filed: Dec. 14, 1988

[51] Int. Cl.⁵ .......................................... A61B 17/00
[52] U.S. Cl. ...................................... 606/1; 606/191
[58] Field of Search .................. 128/303 R, 305, 341, 128/343, 753; 604/36, 73, 48, 54, 93, 171, 264, 275–277, 317, 322, 327, 319, 22; 606/11, 162, 167, 180, 197, 191

[56] References Cited

U.S. PATENT DOCUMENTS

| | | | |
|---|---|---|---|
| 694,541 | 3/1902 | Gordon | 604/39 |
| 1,051,129 | 1/1913 | Lapham | 128/341 |
| 2,749,909 | 6/1956 | Ullery etal. | 128/305 |
| 3,316,912 | 5/1967 | Whitaker | 128/303 R |
| 4,203,444 | 5/1980 | Bonnell et al. | 604/22 |
| 4,228,802 | 10/1980 | Trott | 128/349 R |
| 4,243,037 | 1/1981 | Smith | 128/303 R |
| 4,455,140 | 6/1984 | Joslin | 604/317 |
| 4,596,554 | 6/1986 | Dastgeer | 604/54 |
| 4,649,919 | 3/1987 | Thimsen et al. | 128/305 |
| 4,712,536 | 12/1987 | Hawks | 128/3 |
| 4,728,319 | 3/1988 | Masch | 604/22 |

FOREIGN PATENT DOCUMENTS

| | | | |
|---|---|---|---|
| 130170 | 4/1902 | Fed. Rep. of Germany | 604/1 |
| 3633585 | 4/1988 | Fed. Rep. of Germany | 128/303 R |
| 431351 | 2/1948 | Italy | 128/341 |

*Primary Examiner*—John D. Yasko
*Assistant Examiner*—A. Gutowski
*Attorney, Agent, or Firm*—Gipple & Hale; John S. Hale

[57] ABSTRACT

A medical apparatus for the removal of stool comprising an auger assembly, a helical auger and a hand crank connected to said auger to apply torque to the auger rotatably mounted in a cylindrical connecter housing. A bayonet lock mounted to said connecter housing is adapted to lock and hold a rectal insertion tube in a fixed position. The rectal insertion tube comprising a tube body having a diameter greater than the helix of the auger and has a handle at one end extending therefrom, the other end of the tube body being adapted to be inserted into a rectal ampulla.

8 Claims, 3 Drawing Sheets

DEVICE FOR THE TREATMENT OF FECAL IMPACTION

BACKGROUND OF THE INVENTION

Debilitated and senile patients often have difficulty in moving their bowels primarily because they do not have the strength to sufficiently increase intra abdominal tension by muscular contractions to force the stool from the rectal ampulla. This is not an infrequent occurrence in bedridden patients or patients whose activities are severely restricted so as to make them sedentary and without muscular strength. The inability to evacuate the feces leads to a condition known as fecal impaction. It is especially prevalent in patients in nursing homes. In spite of enemas and cathartics, the inspissated stool in the rectum is still retained because the patient lacks the strength to mold the stool to a size that will traverse the anal sphincter. In these patients it is necessary for a nurse or physician to disempact the stool by extracting the feces bit by bit with a gloved finger inserted into the rectum. This is difficult and time consuming. More importantly, it is uncomfortable and annoying to the patient.

SUMMARY OF THE INVENTION

The present invention describes a hand powered auger apparatus which is inserted into a tube placed in the rectum. The auger apparatus conveys the stool contained in the rectal ampulla into a plastic bag attached to the side of the apparatus.

The apparatus is manufactured of light weight plastic and is designed for single use and discard.

These and other objects and advantages of the present inventive apparatus will become more readily apparent in the following detailed description thereof together with the appended drawings.

DETAILED DESCRIPTION OF THE INVENTION

Figure 1:
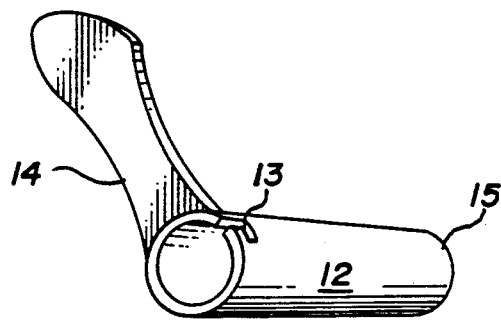
FIG. 1 is a perspective view of a tubular inserter member of the invention.
Figure 2:
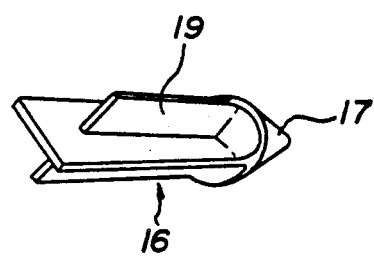
FIG. 2 is a perspective view of an obturator which fits within the inner diameter of the tubular inserter member shown in FIG. 1.
Figure 3:
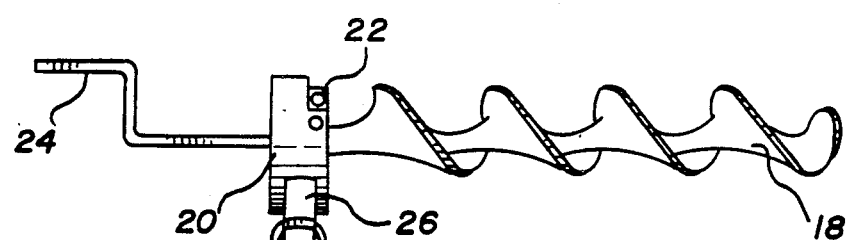
FIG. 3 is a perspective view of the invention showing the auger and connecter housing assembly.
Figure 4:
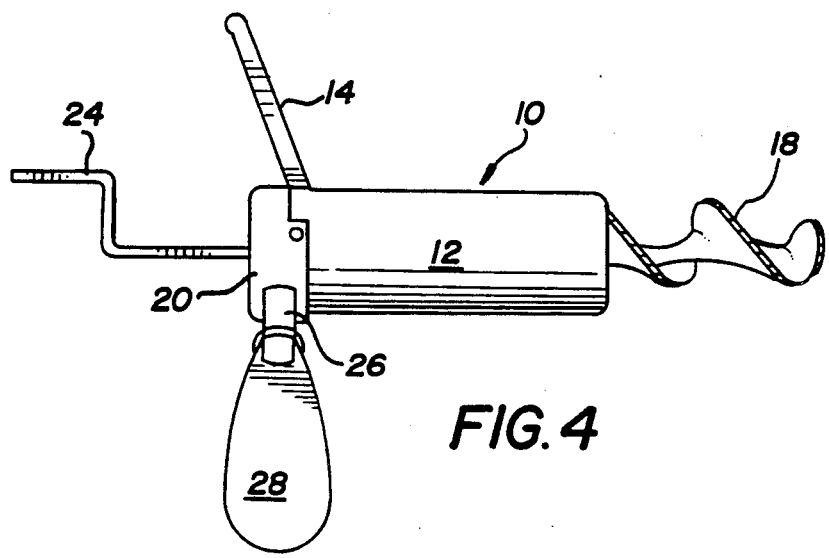
FIG. 4 is a perspective view of the invention showing the auger and connecter housing assembly of FIG. 3 with the tubular inserter member locked onto the connecter housing.

The present inventive apparatus 10 is shown in FIGS. 1 though 4 which is the best mode and preferred embodiment of the invention. The invention uses a circular anoscopic tube inserter member 12 approximately 2.2. centimeters in diameter having a handle 14 which extends angularly from one end of the tube to allow for insertion and removal of the tube. The tube body is formed with a bayonet slot 13 on the same end as handle 14 and holds an obturator 16 with a conical tip 17. The obturator has a planar body 15 with a conical tip 17 on one end and fins 19 which extend away from the conical tip along the planar body perpendicular to the plane of the body. The obturator 16 located at the distal end 15 of the tube allows the tube to be easily introduced into the rectal sphincter 80. After the tube 12 has been introduced into the rectal sphincter, the obturator 16 is removed from the handle end of the tube member and a flexible auger 18 is inserted through the plastic tube so that the feed connecter housing 20 of the auger is turned and locked via bayonet projection 22 into the slot 13 of tube 12 to form a unitary assembly. A crank handle 24 extends through housing 20 and is directly secured to auger 18 to transfer rotational torque from the hand crank to the auger. The auger helix conveys the stool through the tube 12 and into connecter housing 20 where it passes through sleeve 26 into a plastic bag 28. The crank handle 24 makes it simple to turn and advance the auger further into the bowel lumen. When fully introduced into the rectal ampulla, the auger 18 extends approximately 2 inches beyond the opening of the cylindrical tube 12 which acts a container for the auger. The auger is constructed of soft, flexible plastic material so that it cannot injure the bowel wall if it abuts against the same. If the rectal ampulla contain a large amount of feces it may be necessary to move the auger to different positions in the rectal ampulla so as to engage all of the fecal matter. The evacuation of the feces is thus painless and rapid.

Figure 5:
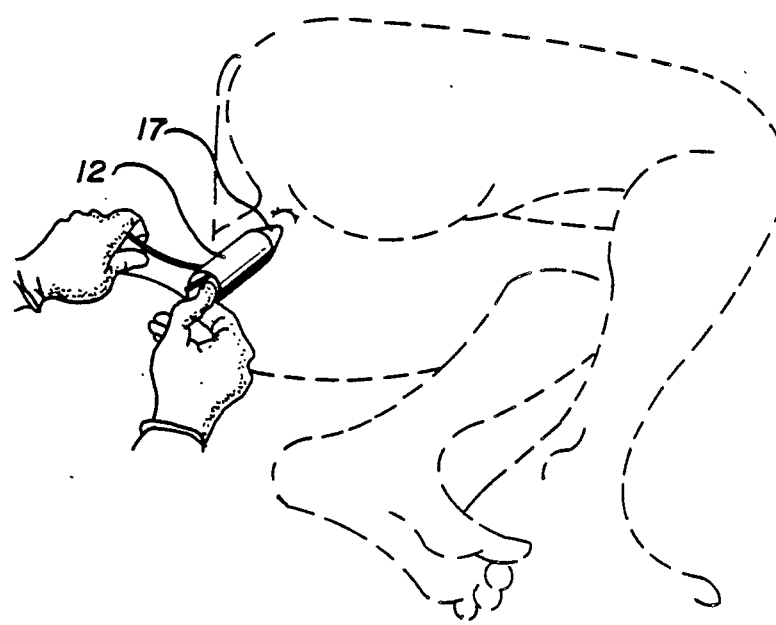
FIG. 5 is a perspective view of the tubular inserter member with an associated obturator being inserted into a rectal ampulla.
Figure 7:
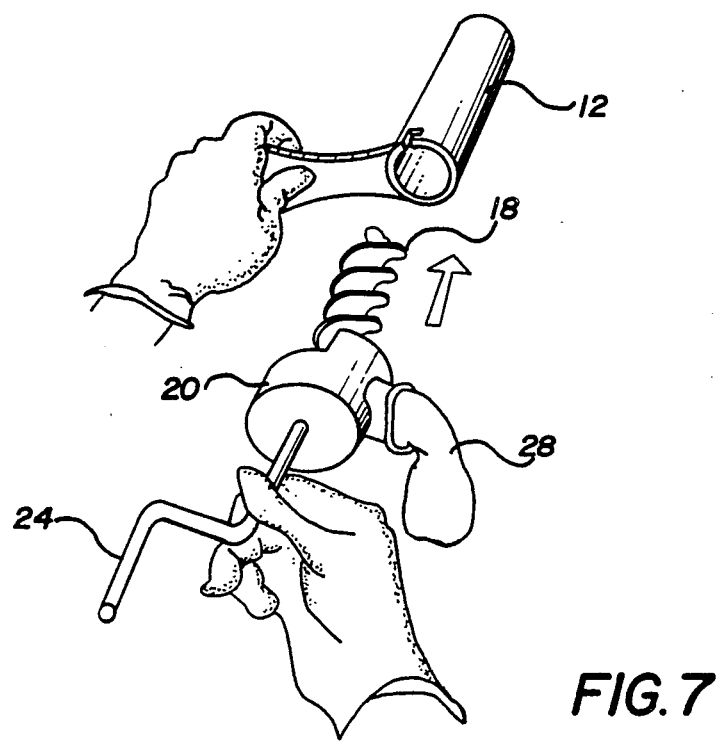
FIG. 7 shows the auger and connecter housing assembly locked to the tubular inserter member.
Figure 6:
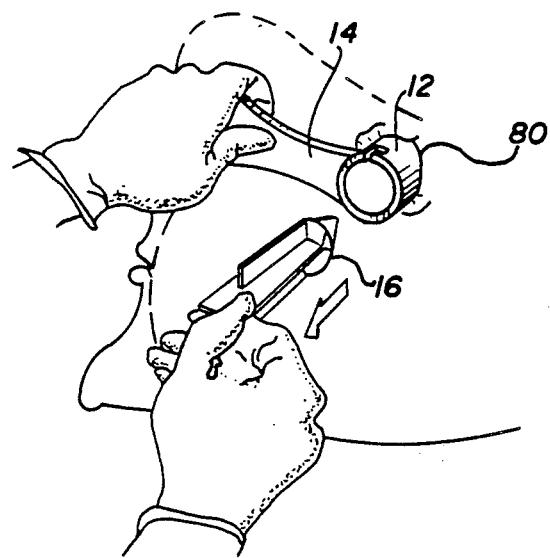
FIG. 6 is an enlarged perspective view of FIG. 5 showing removal of the obturator after the tubular inserter member has been fully introduced into the rectal ampulla.
Figure 8:
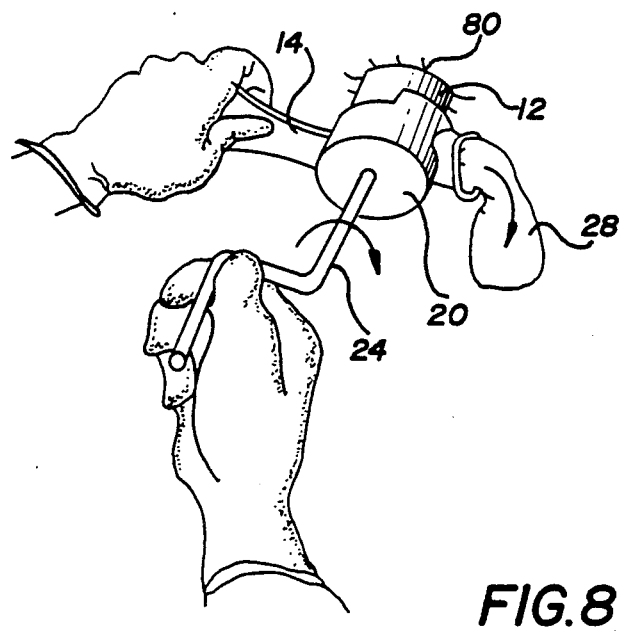
FIG. 8 shows operation of the auger through its cranking handle means to remove stool in the rectal ampulla through the tubular inserter member and into a disposal bag.

In operation as shown in FIGS. 5-7 the obturator 16 with the conical tip 17 is placed inside the cylindrical inserter tube 12 which has a handle 14 angularly extending from one end. The handle 14 is used to hold the tube in the rectum after it is inserted with the conical tipped obturator. Following insertion the obturator is removed and the flexible auger 18 is secured in place on the tube with a bayonet mount and lock. The crank shaft 24 at the end of the auger allows the auger to be rotated into the bowel and retracted as need be. The auger is turned continuously in a circular motion to engage the stool in the rectal ampulla and carry it back through the tube 12, housing 20 and throughgoing sleeve 26 into the plastic bag 28. The plastic bag can be removed if desired; however, the whole apparatus is designed to be a one use disposable medical apparatus.

While a presently preferred form of the present invention has been set further here and above, it is to be understood that the invention is not limited thereby. In particular, the steps of the inventive process are interchangeable, may be interchanged and are equivalent. It is to be understood that the specific details shown are merely illustrative and that the invention may be carried out in other ways without departing from the true spirit and scope of the following claims.

What is claimed is:

1. Apparatus for removing stool comprising auger means, said auger means comprising a flexible auger with a handle means, connector housing mounted to said auger means, said connector housing comprising a cylindrical closed end housing provided with locking means, said locking means being adapted to engage and lock a tube insertion means into a fixed position on said cylindrical housing, said tube insertion means comprising a tube, handle means extending outward at an angle from the axis of the tube and positioned from one end of said tube, stool storage means mounted to said cylindrical housing, said stool storage means comprising a sleeve mounted to said cylindrical housing, said sleeve defining a bore which is throughgoing and communicates with the interior of the cylindrical housing and bag means mounted to said sleeve for holding stool removed and transported by said flexible auger.

2. Apparatus as claimed in claim 1 wherein said bag means comprises a flexible plastic bag with elastic means to securely engage and hold said sleeve.

3. Apparatus as claimed in claim 1 wherein said obturator member has a conical tip.

4. Apparatus as claimed in claim 1 wherein said locking means being adapted to engage and lock a tube insertion means into a fixed position on said cylindrical housing is a bayonet lock.

5. A medical apparatus for the removal of stool comprising a connector housing, an auger means rotatably mounted in said connector housing, said auger means comprising a soft flexible plastic auger and a hand crank connected to said soft flexible plastic auger, lock means mounted to said connector housing, said lock means being adapted to lock and hold a tube insertion means in a fixed position, said tube insertion means comprising a hollow tube body with a handle at one end extending therefrom at an angle from the control axis of the tube, the other end of the tube body being adapted to be inserted into a rectal ampulla and bag means mounted to said connector housing communicating with a chamber formed by said connector housing for holding stool removed and carried by said soft flexible plastic auger.

6. A medical apparatus as claimed in claim 5 including an obturator member adapted to be inserted in said tube insertion means, said obturator member having one end formed with a substantially conical shape.

7. A medical apparatus for the removal of stool comprising a cylindrical connector housing, an auger means rotatably mounted in said connector housing, said auger means comprising a soft flexible helical auger and a hand crank connected to said soft flexible helical auger to apply torque to said soft flexible helical auger, lock means mounted to said connector housing, said lock means being adapted to lock and hold a rectal insertion tube in a fixed position on said connector housing, said rectal insertion tube comprising a hollow tube body having a diameter of approximately 2.2 centimeters which is greater than the helix of the soft flexible helical auger and being provided with a handle at one end extending therefrom, the other end of the tube body being adapted to be inserted into a rectal ampulla and stool storage means mounted to said connector housing for communication with a chamber formed by said connector housing and said tube body to hold stool cut and carried by said soft flexible helical auger.

8. A medical apparatus as claimed in claim 7 including an obturator adapted to be movably mounted in said tube body, said obturator comprising a body, a conical head on one end of said body and fin means extending from said conical head.

* * * * *